United States Patent [19]

Berger et al.

[11] 4,070,495
[45] Jan. 24, 1978

[54] MICROSCOPE SLIDE

[75] Inventors: Dieter Berger, Viernheim; Werner Güthlein, Mannheim-Neckarau; Wolfgang Werner, Mannheim-Vogelstang; Peter Rieckmann, Mannheim-Waldhof, all of Germany

[73] Assignee: Boehringer Mannheim GmbH, Mannheim, Germany

[21] Appl. No.: 672,572

[22] Filed: Mar. 31, 1976

[30] Foreign Application Priority Data

Apr. 11, 1975  Germany .............................. 2515966

[51] Int. Cl.² .................. G01N 33/16; G01N 31/22; G01N 21/60

[52] U.S. Cl. ..................................... 424/3; 23/230 B; 252/408; 427/4

[58] Field of Search ................... 23/230 B, 253 TP; 427/4; 252/408; 424/3

[56] References Cited

U.S. PATENT DOCUMENTS 3,906,120  9/1975  Geating .......................... 23/253 TP Primary Examiner—R.E. Serwin
Attorney, Agent, or Firm—Burgess, Dinklage & Sprung

[57] ABSTRACT

Microscope slide for blood investigation having a coating of highly purified methylene blue N and highly purified cresyl violet acetate in a weight ratio of from 1:1.5 to 1:5.

5 Claims, 2 Drawing Figures

MICROSCOPE SLIDE

BACKGROUND

This invention relates to a pre-colored microscope slide for blood investigations.

The differential blood count is one of the most frequently carried out microscopic methods. In this method, the individual blood particles (erythrocytes, leukocytes, thrombocytes, etc.) are selectively stained with dyestuffs which permit a microscopic differentiation and the recognition of pathological changes. The previously employed staining processes, for example those of Wright, May-Grunwald or Pappenheim, involve several steps, for example, preparing a blood smear, fixing, in some cases several stainings, washing and drying and are, therefore, very laborious. Furthermore, the quality of the staining depends very considerably upon the quality of the dyestuffs employed, as well as upon the training and experience of the personnel involved.

Therefore, attempts have already been made in order to simplify these processes. A process has recently been described in German Pat. No. 2,153,673 which makes use of precolored microscope slides which are coated with methylene blue N and cresyl violet acetate. When a drop of blood is applied to such a microscope slide and covered with a cover slip, then microscopic examination can be carried out after about 5 minutes. In this case, in addition to a differentiation of the various forms of leukocytes and thrombocytes, it is also possible to recognize juvenile erythrocytes, i.e. the so-called reticulocytes. Apart from the simplicity and accuracy of use, this is a further advance in comparison with the conventional blood count.

In spite of the undeniable advantage provided by this process, nevertheless it suffers from some serious disadvantages. Thus, the stainings are generally dull, diffuse and lacking in contrast and, in addition, the three different forms of the granulated leukocytes (eosinophils, neutrophils and basophils) can only be differentiated with difficulty.

SUMMARY

It has now been found that pre-colored microscope slides can be obtained which give high contrast and luminescent stainings and which permit and accurate differentiation of the granulocytes when the dyestuffs methylene blue N and cresyl violet acetate are used in highly purified form in a weight ratio of 1:1.5 to 1:5.

DESCRIPTION OF THE DRAWING

In the accompanying drawing.

DESCRIPTION

Figure 1A:
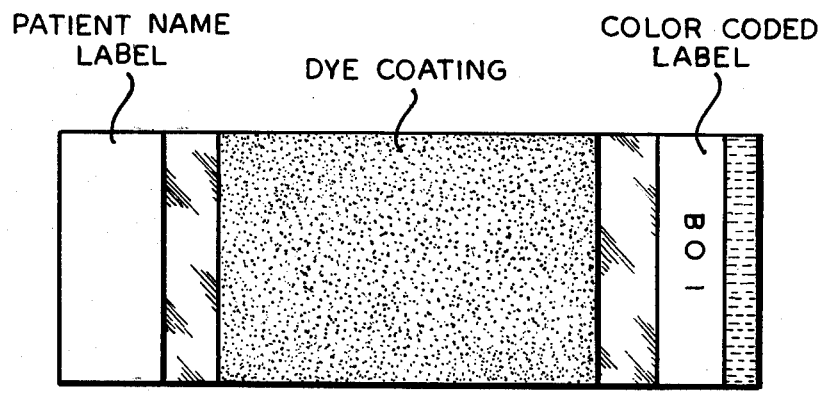
FIG. 1a and 1b are top plane and side views, respectively, of a microscopic slide according to the invention.
Figure 1B:
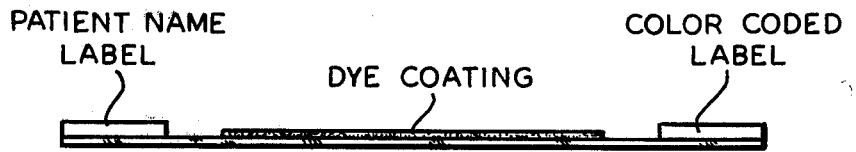

The methylene blue N is preferably used in the form of its monohydrochloride instead of the commercially available zinc double salt.

The above-mentioned German Pat. No. 2,153,673 gives no indication of the quality of the dyestuffs used. The fact that, in the preparation of the dyestuff solutions, insoluble residues are to be filtered off, indicates that the dyestuffs employed are of commercial quality. In fact, upon repetition of the disclosures in this German patent using commercially available dyestuffs, pre-colored microscope slides are obtained, the staining properties of which correspond to those of this German Patent (see pages 5 -6 thereof).

Purification of dyestuffs for microscopy is generally not usual. Thus, for many decades, dyestuffs have been used of doubtful purity which otherwise are only employed for dyeing textiles. Furthermore, in the case of many dyestuffs, it is not known whether and which impurities influence the staining result. Thus, for example, it is not surprising that the American Biological Stain Commission considers, as the most important criterion in the specificaition of a dyestuff, the usefulness in certain dyestuff formulations and, for the determination of content, merely prescribes photometric and reductometric methods but not chromatographic methods (of, for example R.D. Lillie, "Conn's Biological Stains", 8th ed., pub. Williams and Wilkins Comp., Baltimore, U.S.A., 1969, pp. 10 - 14 and 416 - 417).

However, these photometric and reductometric methods only permit, at most, conclusions regarding the total dyestuff content but not of any coloring impurities which may possibly be present.

Methylene blue N (new methylene blue, C.I. Basic Blue 24, 3,7-bis-(N-ethylamino)-2,8-dimethylphenothiazonium chloride) is commercially available in about 50 - 70% purity and, according to our own findings, thin layer chromatographic analysis shows three to four additional spots in varying amounts. The remainder is zinc chloride and sodium chloride. We have also found that an excellent purification of methylene blue N can be carried out by dissolving this dyestuff in water and precipitating out the hydrochloride thereof with hydrochloric acid. There is thus obtsined a chormatographically pure product which only contains about 0.5% zinc chloride and is in the form of the monohydrochloride.

Cresyl violet acetate (Cresylechtviolett, Cresyl Fast Violet acetate, 5,9-diaminobenzo (a)phenoxazonium acetate) is commercially available, contaminated with more or less large amounts of sodium acetate. In this case, too, thin layer chromatographic analysis shows three additional spots in varying amounts. Purification of this dyestuff can be carried out in the following manner: The sodium acetate is first removed by careful digestion with water. Thereafter, the dyestuff is dissolved in methanol and precipitated out with diethyl ether. Repetition of this procudure gives a chromatographically pure product.

In contradistincitio to the commerically available products, the dyestuffs purified in the above-described manner dissolve in methanol without leaving a residue and can be applied to microscope slides in the manner described on page 4 of the above-mentioned German Pat. No. 2,153,673. Furthermore, according to the teachings in German Pat. No. 2,424,955, they can be dissolved in water and applied, together with polyoxyethylene-sorbitan monopalmitate (Tween 80)

Furthermore, it is astonishing that useful microscope slides with surprisingly improved properties are only obtained when the ratio of the two dyestuffs is from 1:1.5 to 1:5. Thus, in German Pat. No. 2,153,673 it is, in contradistinction thereto, asseted that the ratio is to be 3:1 and in German Pat. No. 2,424,955 that the ratio is to be 2.5:1 and that significant variations are to be avoided as far as possible.

According to a preferred embodiment of the present invention, the dyestuff solutions are sprayed on to microscope slides in the manner described in co-pedning application Ser. No. 672,574 filed Mar. 31, 1976 (German Patent Application No. P 25 15 869.4).

The purified dyestuffs are preferably applied to the microscope slides in total amounts of about 0.5 to 10γ/cm². The ratio of methylene blue N to cresyl violet acetate may thereby vary between the values of 1:1.5 to 1:5.

The pre-coated microscope slides according to the present invention can, as described on pages 4 to 5 of German Pat. No. 2,153,673, be provided with a drop of blood and then covered with a cover slip; after about 3 to 5 minutes, microscopic examination can be carried out witha an oil immersion objective.

The stainings obtained are extraordinarily clear, have a high degree of contrast and are readily reproducible. In contradistinction to the staining characteristics described on pages 5 – 6 of German Pat. No. 2,153,673, the following special characteristics are to be observed:

a. The granula of the eosinophils have a luminescent yellow color, in comparison with the there-described orange coloration.

b. The granula of the basophils are orange-red colored, in comparison with the there-described purple coloration. The orange coloration, which is the most effectively identifiable characteristic, there only occurs on the edge of the cells in the case of suitable focussing.

c. The contours of the nuclei are extremely clearly recognizable, which considerably simplifies the differentiation of lymphocytes, monocytes and the various stages of maturity of the granulocytes.

A further advantage of the microscope slides according to the present invention is that the stainings no longer depend upon variations of quality of commercially available dyestuffs. In the case of the large-scale production of large numbers of microscope slides, the reproducibility with regard to dyestuff application and composition is of the greatest possible importance.

The microscope slides can be made from glass. However, insofar as the dyestuffs are sprayed on in the manner described in co-pending Application Ser, No. 672,574 (German Patent Application No. P 25 15 869.4), synthetic resin microscope slides can also be used, whereby the dyestuff can, of course, also be applied to cover slips made from glass or synthetic resin.

The following Examples are given for the purpose of illustrating the present invention:

EXAMPLE 1

Purification of cresyl violet acetate 50 g. cresyl violet acetate (obtained from Matheson, Coleman & Bell) were suspended in 100 ml. water and vigorously stirred for 15 minutes. Thereafter, the dyestuff was filtered off with suction and washed twice with 100 ml. amounts of ice-cold water. The filter residue was dissolved, with warming, in 1.6 liters methanol and insoluble material removed by suction filtration at about 30° C. The filtrate was slowly mixed, while stirring, with 3.5 liters diethyl ether and then further stirred for 30 minutes, while cooling with ice. The crystals formed were filtered off with suction, dissolved, with warming, in 620 ml. methanol and the solution is cooled to 30° C. The dyestuff was precipitated out by the addition of 1.85 liters diethyl ether, while stirring and cooling with ice. After filtering off with suction and washing three times with 120 ml. amounts of diethyl ether-methanol (3:1), there were obtained, after drying over phosphorus pentoxide, 22 g. cresyl violet acetate in the form of dark green crystals. This product contains, by weight, about 82% violet acetate, 8% cresyl violet chloride and 10% water. Upon heating to 150° C., decomposition occurs. According to chromatographic investigation (DC finished plate, silica gel 60 F 254, Merck; elution agent system n-butanol-glacial acetic acid-water 4:1:5), the substance was practically pure; $R_F$ value: 0.6.

EXAMPLE 2

Purification of methylene blue N 100 g. methylene blue N (New Methylene Blue) (obtained from Matheson, Coleman & Bell) were dissolved in 1 liter water in a 4 liter three-necked flask and mixed with 1 liter concentrated hydrochloric acid (d = 1.18). After stirring for 4 hours, while cooling with ice, followed by standing for 8 hours in a refrigerator at +5° C., the crystals formed were filtered off with suction, washed with 400 ml. ice-cooled 6N hydrochloric acid and 500 ml. diethyl ether. There were obtained 36.5 g. black, metallically glossy crystals which decompose from 253° C. The purified dyestuff contains, by weight, 95 – 97% methylene blue N chloride hydrochloride, as well as 3 – 5% water. Zinc was only present in traces. According to chromatographic investigation (DC finished plate silica gel 60 F 254, Merck; elution agent system n-butanol-glacial acetic acid-water 4:1:5), the dyestuff was practically pure; $R_F$ value: 0.5)

EXAMPLE 3

Pre-colored microscope slide

A solution was prepared of the following composition, using the purified dyestuffs according to Examples 1 and 2:

methylene blue N hydrochoride:130 mg.
cresyl violet acetate:270 mg.
methanol:ad 100 ml.

This solution was coated as a film, using a swab of cottonwool, on to a microscope slide and then dried or was sprayed from a 0.5 mm. wide spray nozzle (SS 60 67228-45 of the firm Spraying Systems) with a spraying angle of about 25° at a distance of 20 cm. through a mask in a breadth of 3 cm. on to a microscope slide which passed below the nozzle at a speed of 1.5 meters/minute. The spray pressure was 1.2 ats. and the rate of flow through the nozzle was 10 ml./minute.

In the case of an average droplet size of about 20μ, the amount of dyestuff applied is about 3 μg./cm².

A drop of blood with a volume of about 5 – 10 μl. was applied to the pre-colored microscope slide and then covered with a cover slip. After about 3 to 5 minutes, the staining was assessed under a microscope at about 800 fold magnification, using an oil immersion objective.

The individual particles of the blood have the following stainings:

reticulocytes : purple-colored reticulum within the scarcely colored erythrocytes.
neutrophils : purple-colored nucleus within a fine granulated, almost colorless plasma.
eosinophils : purple-colored nucleus within a coursely granulated yellow plasma.
basophils : dark purple-colored nucleus within an average-sized, compact granulated orange-red colored plasma.
lymphocytes : purple-colored nucleus with bright purple-colored plasma.

monocytes : like lymphocytes but larger and with more plasma.

thrombocytes : small purple-colored particles.

What is claimed is:

1. Microscope slide for blood investigation comprising a coating of chromatographically pure methylene blue N and cresyl violet acetate in a weight ratio of from 1:1.5 to 1:5.

2. Microscope slide of claim 1 wherein the methylene blue N is present as the monohydrochloride.

3. Microscope slide of claim 1 wherein the dyestuffs are applied by spraying a solution thereof.

4. Use of chromatographically pure methylene blue N and cresyl violet acetate in a weight ratio of from 1:1.5 to 1:5 for the production of pre-colored microscope slides for blood investigation.

5. Improved process for blood investigation wherein chromatographically pure methylene blue N and cresyl violet acetate in a weight ratio of from 1:1.5 to 1:5 are used on pre-colored microscope slides.

* * * * *